(12) United States Patent
Dowaki

(10) Patent No.: US 9,354,184 B2
(45) Date of Patent: May 31, 2016

(54) IMAGING APPARATUS, X-RAY DETECTOR, AND IMAGING METHOD

(71) Applicant: CANON KABUSHIKI KAISHA, Tokyo (JP)

(72) Inventor: Kanako Dowaki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 161 days.

(21) Appl. No.: 13/753,873

(22) Filed: Jan. 30, 2013

(65) Prior Publication Data

US 2013/0193334 A1     Aug. 1, 2013

(30) Foreign Application Priority Data

Feb. 1, 2012    (JP) ................. 2012-020030

(51) Int. Cl.
| | |
|---|---|
| H01L 27/146 | (2006.01) |
| G01N 23/04 | (2006.01) |
| G01T 1/24 | (2006.01) |
| H04N 5/32 | (2006.01) |
| H04N 5/345 | (2011.01) |
| H04N 5/347 | (2011.01) |
| H04N 5/355 | (2011.01) |
| H04N 5/361 | (2011.01) |
| H04N 5/363 | (2011.01) |

(52) U.S. Cl.
CPC *G01N 23/04* (2013.01); *G01T 1/24* (2013.01); *H04N 5/32* (2013.01); *H04N 5/345* (2013.01); *H04N 5/347* (2013.01); *H04N 5/3559* (2013.01); *H04N 5/361* (2013.01); *H04N 5/363* (2013.01)

(58) Field of Classification Search
CPC ..... H04N 5/367; H04N 5/346; H04N 5/2178; H04N 5/378; H04N 5/3575

USPC ...................................... 250/370.09
See application file for complete search history.

(56) References Cited

U.S. PATENT DOCUMENTS

| | | | |
|---|---|---|---|
| 5,467,380 A | 11/1995 | De Jonge et al. | |
| 7,265,784 B1 * | 9/2007 | Frank | H04N 5/2351 348/222.1 |
| 2002/0190215 A1 | 12/2002 | Tashiro | |

(Continued)

FOREIGN PATENT DOCUMENTS

| | | |
|---|---|---|
| CN | 1764244 A | 4/2006 |
| EP | 1335588 A1 | 8/2003 |
| JP | 2002344809 A | 11/2002 |
| JP | 2006319529 A | 11/2006 |

(Continued)

*Primary Examiner* — David J Makiya
*Assistant Examiner* — Kenneth J Malkowski
(74) *Attorney, Agent, or Firm* — Canon USA Inc., IP Division

(57) ABSTRACT

An imaging apparatus includes a sensor including a plurality of pixels arranged in a two-dimensional pattern, a sample-hold unit configured to sample and hold a signal obtained from each pixel, and a reading unit configured to perform scanning in such a way as to perform a plurality of non-destructive reading operations for pixels of one row and as to read pixels of the next row, and to subsequently perform scanning in a row direction and a column direction to read the signal having been sampled and held by the sample-hold unit, an A/D conversion unit configured to perform analog/digital conversion processing on the signal read by the reading unit, an averaging processing unit configured to perform averaging processing on the signal converted by the A/D conversion unit, for each pixel, and a digital binning unit configured to perform binning processing using the signal processed by the averaging processing unit.

22 Claims, 11 Drawing Sheets

(56) References Cited

U.S. PATENT DOCUMENTS

2008/0117318 A1* 5/2008 Aoki .................... 348/246
2008/0273101 A1* 11/2008 Takenaka et al. ........... 348/243
2009/0021607 A1* 1/2009 Takenaka et al. ........ 348/231.99
2010/0072350 A1* 3/2010 De Wit et al. ............. 250/208.1
2012/0006993 A1 1/2012 Arishima et al.

FOREIGN PATENT DOCUMENTS

| | | | |
|---|---|---|---|
| JP | 2009-049527 | A | 3/2009 |
| JP | 2009159497 | A | 7/2009 |
| JP | 2011013180 | A | 1/2011 |
| JP | 2011-171950 | A | 9/2011 |

\* cited by examiner

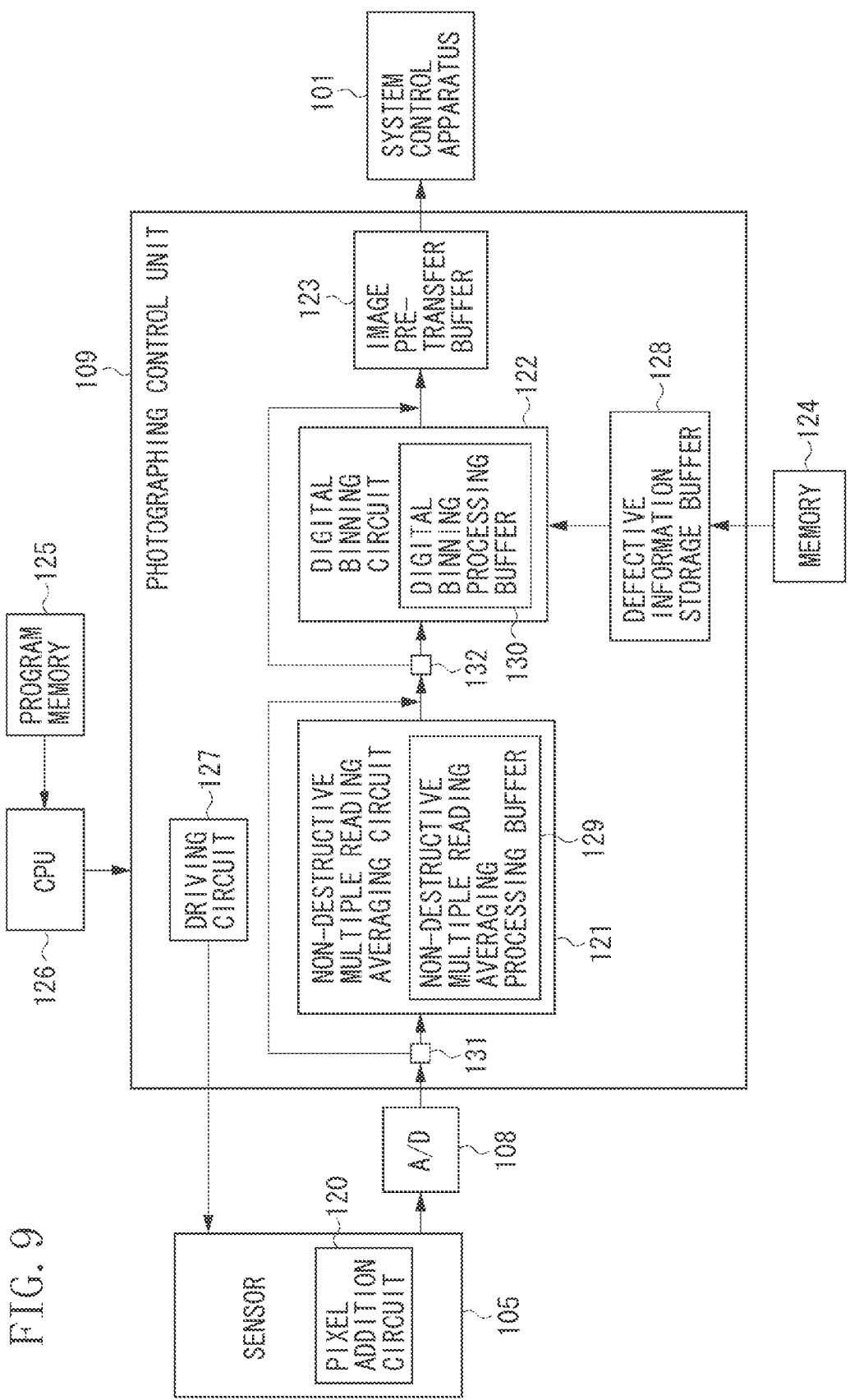

IMAGING APPARATUS, X-RAY DETECTOR, AND IMAGING METHOD

BACKGROUND

1. Field of the Invention

The present invention relates to an imaging apparatus, an X-ray detector, and an imaging method.

2. Description of the Related Art

In the field of digital radiation imaging apparatuses, an equal-magnification optical system large-area flat panel type sensor using a photoelectric conversion element, instead of using an image intensifier, is widely used to improve the resolution, reduce the size, or suppress distortions of an image.

As discussed in Japanese Patent Application Laid-Open No. 2002-344809, it is conventionally proposed to realize a sufficiently large area of a flat panel type sensor by tiling a plurality of rectangular semiconductor substrates, which can be cut away from a silicon semiconductor wafer. A plurality of complementary metal oxide semiconductor (CMOS)-type image sensors is formed as photoelectric conversion elements on the obtained rectangular semiconductor substrate. The CMOS-type image sensor can realize high-speed reading, when the micromachining technique is employed, compared to an amorphous silicon type sensor. Further, the CMOS-type image sensor has high sensitivity. It is easy for the CMOS-type image sensor to obtain a large area compared to a case where a charge coupled device (CCD)-type image sensor is used.

Further, as discussed in Japanese Patent Application Laid-Open No. 2006-319529, it is conventionally known that an imaging apparatus can be configured to have a pixel addition function to perform binning processing for adding signals from a plurality of neighboring pixels, as a signal of one pixel. When reduction processing is performed based on the binning processing, an image having been subjected to the reduction processing may deteriorate due to the presence of a defective pixel. To solve this problem, it is useful to perform the processing without including any pixel signal of the defective pixel.

Further, a signal read from an image sensor includes random noises, such as thermal noises of an amplifier that reads the signal from the image sensor and disturbance noises of electronic devices. As a method capable of reducing the above-described random noises, it is conventionally known to read a signal stored during a single exposure operation plural times using an image sensor that has the capability of realizing a non-destructive signal reading operation and obtaining an average of the readout signals to reduce randomly generating noises.

It may be possible to perform the binning processing considering the presence of defective pixels together with addition processing of signals obtained in a plurality of non-destructive reading operations. In this case, if averaging processing of respective pixels is performed after completion of the binning processing considering the presence of defective pixels, it is required to perform the binning processing as much as frames having been non-destructively read out. For example, in a case where defective pixel positional information to be referred to in the binning processing is read out from an external memory in parallel with the binning processing, the processing speed tends to decrease because of an increase in the number of times the memory is accessed in addition to the number of times the binning processing is performed.

SUMMARY

The present invention is directed to an imaging apparatus. According to some embodiments of the present invention, an imaging apparatus includes a sensor including a plurality of pixels arranged in a two-dimensional pattern, a sample-hold unit configured to sample and hold a signal obtained from each of the plurality of pixels, and a reading unit configured to perform scanning in such a way as to perform a plurality of non-destructive reading operations for pixels of one row and as to read pixels of the next row, and to subsequently perform scanning in a row direction and a column direction to read the signal having been sampled and held by the sample-hold unit, an A/D conversion unit configured to perform analog/digital conversion processing on the signal read by the reading unit, an averaging processing unit configured to perform averaging processing on the signal having been analog/digital converted by the A/D conversion unit, for each pixel, and a digital binning unit configured to perform binning processing using the signal having been averaging processed by the averaging processing unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 9 illustrates a configuration example of a flat panel sensor and a photographing control unit according to the present exemplary embodiment.

DESCRIPTION OF THE EMBODIMENTS

Various exemplary embodiments, features, and aspects of the invention will be described in detail below with reference to the drawings.

Figure 1:
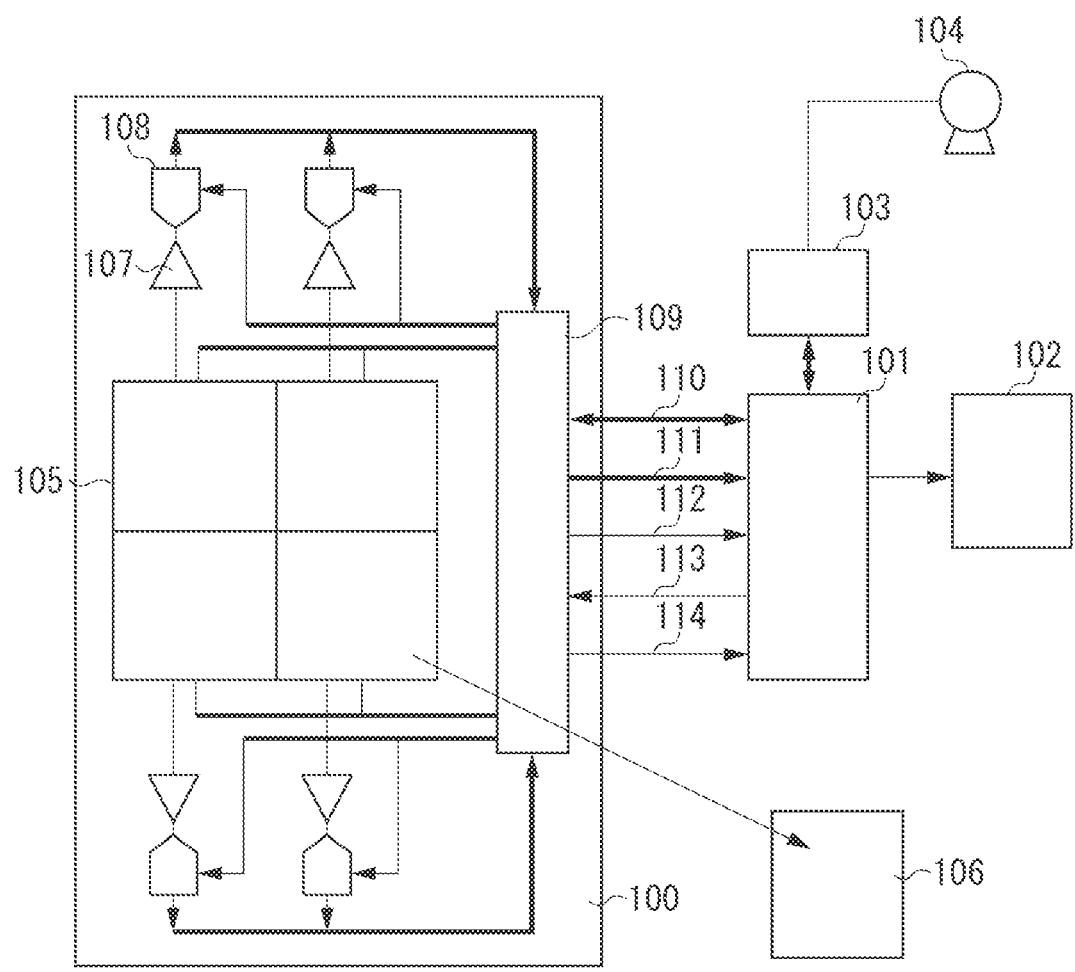
FIG. 1 illustrates a configuration example of an imaging system that includes an imaging apparatus according to an exemplary embodiment of the present invention.

FIG. 1 is a block diagram illustrating a configuration example of an imaging system that includes an imaging apparatus according to an exemplary embodiment of the present invention. FIG. 1 schematically illustrates an entire configuration of a large-area flat panel type radiation moving image capturing system.

The imaging system illustrated in FIG. 1 includes a radiation imaging apparatus 100, a system control apparatus 101 including an image processing unit, an image display apparatus 102, a radiation generation apparatus 103, and a radiation source 104. In a photographing operation performed by the imaging system illustrated in FIG. 1, the radiation imaging apparatus 100 and the radiation generation apparatus 103 are synchronously controlled by the system control apparatus 101.

A radiation having passed through a subject is converted into visible light by a scintillator (not illustrated) and then photoelectrically converted. A photoelectrically converted signal that represents the quantity of light is then analog/digital (A/D) converted. Further, the A/D converted signal is transferred, as frame image data that corresponds to the irradiated radiation, from the radiation imaging apparatus 100 to the image processing unit in the system control apparatus 101. A radiation image, after having being subjected to the image processing, can be displayed in real time on the image display apparatus 102. In the present exemplary embodiment, the radiation imaging apparatus 100 is functionally operable as an X-ray detector.

The radiation imaging apparatus 100 includes a flat panel sensor 105. The flat panel sensor 105 includes a plurality of pixels arranged in a two-dimensional pattern. Each pixel includes a photoelectric conversion element and a sample-hold circuit. The sample-hold circuit can sample and hold a signal received from the photoelectric conversion element. The flat panel sensor 105 includes a plurality of rectangular semiconductor substrates 106 tiled in a matrix pattern on a planar substrate (not illustrated). A CMOS-type image sensor (serving as the photoelectric conversion element), which can be cut away from a silicon semiconductor wafer, is formed on each rectangular semiconductor substrate 106. Each rectangular semiconductor substrate 106 is usable as a connecting area sensor, and includes a plurality of CMOS-type image sensors that is arranged at equal pitches to form a two-dimensional pattern.

The flat panel sensor 105 and the above-described scintillator cooperatively constitute an X-ray image sensor that can acquire an image based on the detected X ray. Further, two neighboring rectangular semiconductor substrates 106 are tiled on the planar substrate in such a way that the photoelectric conversion elements are disposed at equal pitches beyond the boundary between the rectangular semiconductor substrates 106.

The flat panel sensor 105 illustrated in FIG. 1 includes four rectangular semiconductor substrates 106 tiled in a matrix pattern of two columns×two rows. However, the flat panel sensor 105 is not limited to the above-described example. The number of rectangular semiconductor substrates 106 to be tiled in the row direction and the number of rectangular semiconductor substrates 106 to be tiled in the column direction are arbitrary.

Although not illustrated in the drawing, external terminals (electrode pads) of the rectangular semiconductor substrates 106 arranged in the matrix pattern are disposed along an upper periphery and a lower periphery of the flat panel sensor 105. The electrode pads of the rectangular semiconductor substrates 106 are connected to an external circuit via a flying lead type printed-wiring board (not illustrated). Switching elements, such as analog switching elements each capable of switching the enable/disable state of an analog output, are provided on each rectangular semiconductor substrate 106.

When the analog output switching elements are provided, an output control of the rectangular semiconductor substrate 106 based on a chip select control signal can be realized. Analog output lines of the rectangular semiconductor substrate 106 can be united together and directly connected to an amplifier 107. A single rectangular semiconductor substrate 106 tiled on the flat panel sensor 105 serves as a conversion region of one A/D converter 108, in which a signal from the pixel can be analog/digital converted.

A photographing control unit 109 can communicate with the system control apparatus 101 with respect to control commands and synchronous signals, and can transmit image data to the image processing unit in the system control apparatus 101. The photographing control unit 109 has the capability of controlling the flat panel sensor 105. For example, the photographing control unit 109 can perform drive control or photographing mode control for the flat panel sensor 105.

For example, the photographing control unit 109 performs control to perform a plurality of non-destructive reading operations for signals having been sampled and held from photoelectric conversion elements of one row and subsequently perform a plurality of non-destructive reading operations for pixels of the next row. Further, the photographing control unit 109 combines digital image data of each block having been A/D converted by a plurality of A/D converters 108 provided in the radiation imaging apparatus 100 with frame data, and transfers the combined data to the image processing unit in the system control apparatus 101.

A command control dedicated interface 110 enables the photographing control unit 109 to communicate with the system control apparatus 101 to receive a photographing mode setting, various parameter settings, a photographing start setting, and a photographing termination setting. Further, the photographing control unit 109 can transmit an operational state of the radiation imaging apparatus 100 to the system control apparatus 101 via the command control dedicated interface 110.

An image data interface 111 enables the photographing control unit 109 to transmit image data, if it has been obtained in a photographing operation, to the system control apparatus 101. The photographing control unit 109 can transmit a READY signal 112, which indicates that the radiation imaging apparatus 100 is ready to perform a photographing operation, to the system control apparatus 101.

In response to a reception of the READY signal 112 from the photographing control unit 109, the system control apparatus 101 can transmit an external synchronous signal 113, which informs radiation exposure timing, to the photographing control unit 109. The photographing control unit 109 can transmit an exposure allowance signal 114 to the system control apparatus 101. An exposure signal can be transmitted from the system control apparatus 101 to the radiation generation apparatus 103 when the exposure allowance signal 114 is in an enable state. The radiation having been emitted from the radiation source 104 is stored as effective radiation, and an X-ray image can be formed.

Figure 2:
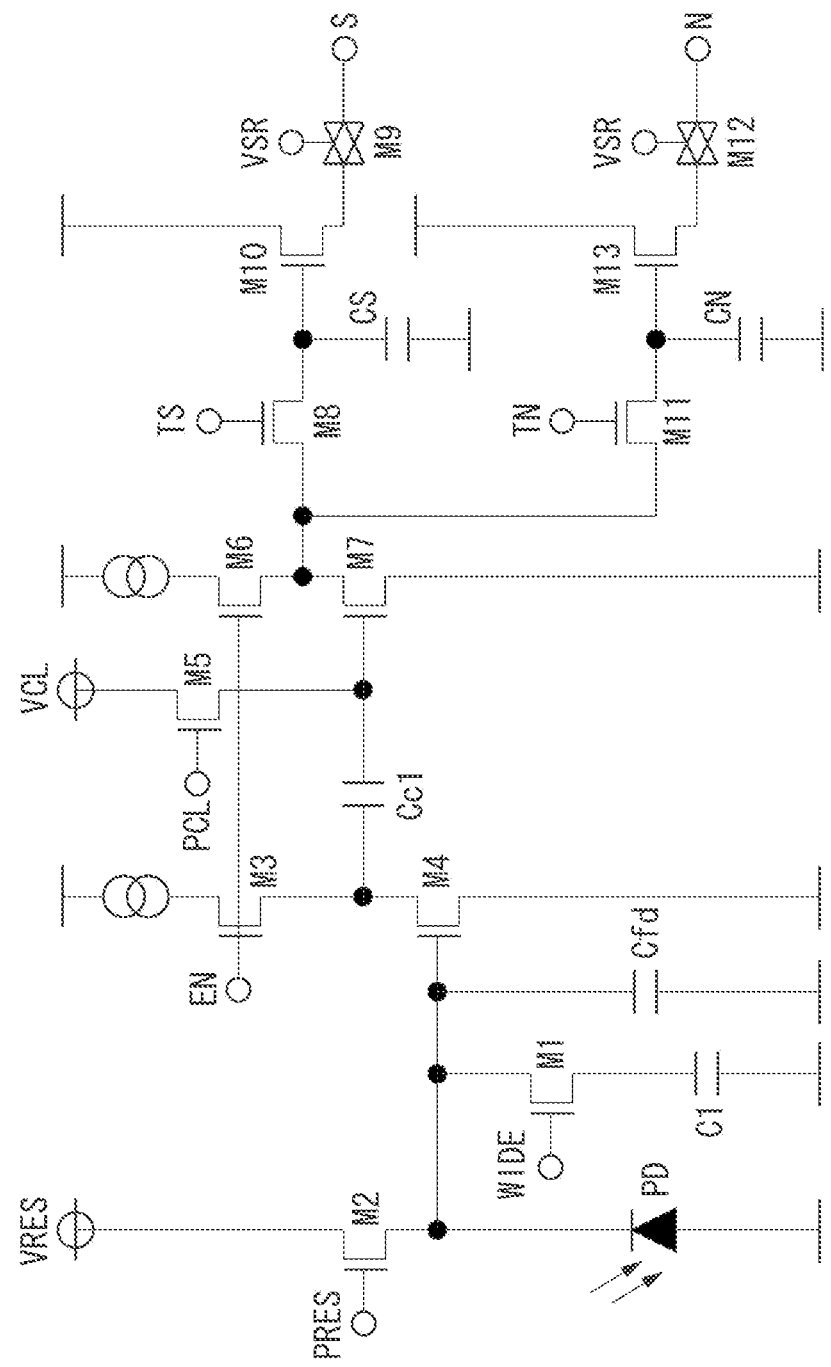
FIG. 2 illustrates a configuration example of a pixel circuit according to the present exemplary embodiment.

FIG. 2 illustrates a configuration example of a pixel circuit. The pixel circuit illustrated in FIG. 2 corresponds to one of a plurality of pixels arranged in a two-dimensional pattern on the rectangular semiconductor substrate 106.

In the pixel circuit illustrated in FIG. 2, a photo diode (PD) can perform photoelectric conversion. A reset MOS transistor M2 is operable as a reset switch that can discharge electric charges stored in a floating diffusion (i.e., floating diffusion region) capacitor Cfd.

Further, a sensitivity switching MOS transistor M1 is operable as a sensitivity selection switch that can select a high dynamic range mode or a high sensitivity mode. A dynamic range enlargement capacitor C1 can store electric charges when the sensitivity selection switch (M1) is turned on. Capacity of a floating node region substantially increases when the sensitivity selection switch (M1) is turned on. Therefore, the dynamic range can be enlarged although the sensitivity is lowered.

Accordingly, for example, the sensitivity selection switch (M1) is turned off in a penetrative photographing operation because high sensitivity is required. On the other hand, the sensitivity selection switch (M1) is turned on in a digital subtraction angiography (DSA) photographing operation because a high dynamic range is required.

An amplification MOS transistor M4 is operable as a first pixel amplifier that can serve as a source follower. A selection MOS transistor M3 is operable as a first selection switch that can bring the first pixel amplifier (M4) into an operational state.

A clamp circuit that can remove kTC noises generated from photoelectric conversion regions is provided in such a way as to follow the first pixel amplifier (M4). The clamp circuit includes a clamp capacitor Ccl and a clamping dedicated MOS transistor M5 that is operable as a clamp switch. An amplification MOS transistor M7 is operable as a second pixel amplifier that can serve as a source follower. A selection MOS transistor M6 is operable as a second selection switch that can bring the second pixel amplifier (M7) into an operational state.

An optical signal dedicated sample-hold circuit and a noise signal dedicated sample-hold circuit are provided in such a way as to follow the second pixel amplifier (M7). A sample-hold MOS transistor M8 is operable as an optical signal dedicated sample-hold switch that constitutes an optical signal storage sample-hold circuit. The optical signal dedicated sample-hold circuit includes an optical signal holding capacitor CS.

A sample-hold MOS transistor M11 is operable as a noise signal dedicated sample-hold switch N that constitutes a noise signal storage sample-hold circuit. The noise signal dedicated sample-hold circuit includes a noise signal holding capacitor CN.

An optical signal amplification MOS transistor M10 is operable as an optical signal dedicated pixel amplifier that can serve as a source follower. An analog switch M9 is operable as an optical signal transfer switch that can output an optical signal amplified by the optical signal dedicated pixel amplifier (M10) to an S signal output line.

A noise signal amplification MOS transistor M13 is operable as a noise signal dedicated pixel amplifier that can serve as a source follower. An analog switch M12 is operable as a noise signal transfer switch that can output a noise signal amplified by the noise signal dedicated pixel amplifier (M13) to an N signal output line.

An enable signal EN is connected to a gate of the first selection switch (M3) and a gate of the second selection switch (M6). The enable signal EN is a control signal that can bring each of the first pixel amplifier (M4) and the second pixel amplifier (M7) into an operational state. When the enable signal EN is a high-level signal, the first pixel amplifier (M4) and the second pixel amplifier (M7) are simultaneously operable.

A control signal WIDE is connected to a gate of the sensitivity selection switch (M1). The control signal WIDE can control the switching of sensitivity. When the control signal WIDE is a low-level signal, the sensitivity selection switch (M1) turns off to select the high sensitivity mode.

A reset signal PRES can turn on the reset switch (M2) to discharge the electric charges stored in the photo diode PD. A clamp signal PCL can control the clamp switch (M5). When the clamp signal PCL is a high-level signal, the clamp switch (M5) turns on to set the clamp capacitor (Ccl) to a reference voltage VCL.

A signal TS is an optical signal sample-hold control signal. When the signal TS is a high-level signal, the optical signal dedicated sample-hold switch (M8) turns on to perform batch transmission of the optical signal to the capacitor CS via the second pixel amplifier (M7). Then, bringing the signal TS into a low level in a lump sum for all of the pixels to turn off the optical signal dedicated sample-hold switch (M8) completes the storage of optical signal charges to the sample-hold circuit.

A signal TN is a noise signal sample-hold control signal. When the signal TN is a high-level signal, the noise signal dedicated sample-hold switch (M11) turns on to perform batch transmission of the noise signal to the capacitor CN via the second pixel amplifier (M7). Then, bringing the signal TN into a low level in a lump sum for all of the pixels to turn off the noise signal dedicated sample-hold switch (M11) completes the storage of noise signal charges to the sample-hold circuit.

The optical signal dedicated sample-hold switch (M8) and the noise signal dedicated sample-hold switch (M11) turn off after the sample-hold processing of the capacitor CS and the capacitor CN. The capacitor CS and the capacitor CN are electrically separated from a forward-stage storage circuit. Therefore, it is possible to non-destructively read the optical signal and the noise signal having been stored before the sampling operation is performed again.

Figure 3:
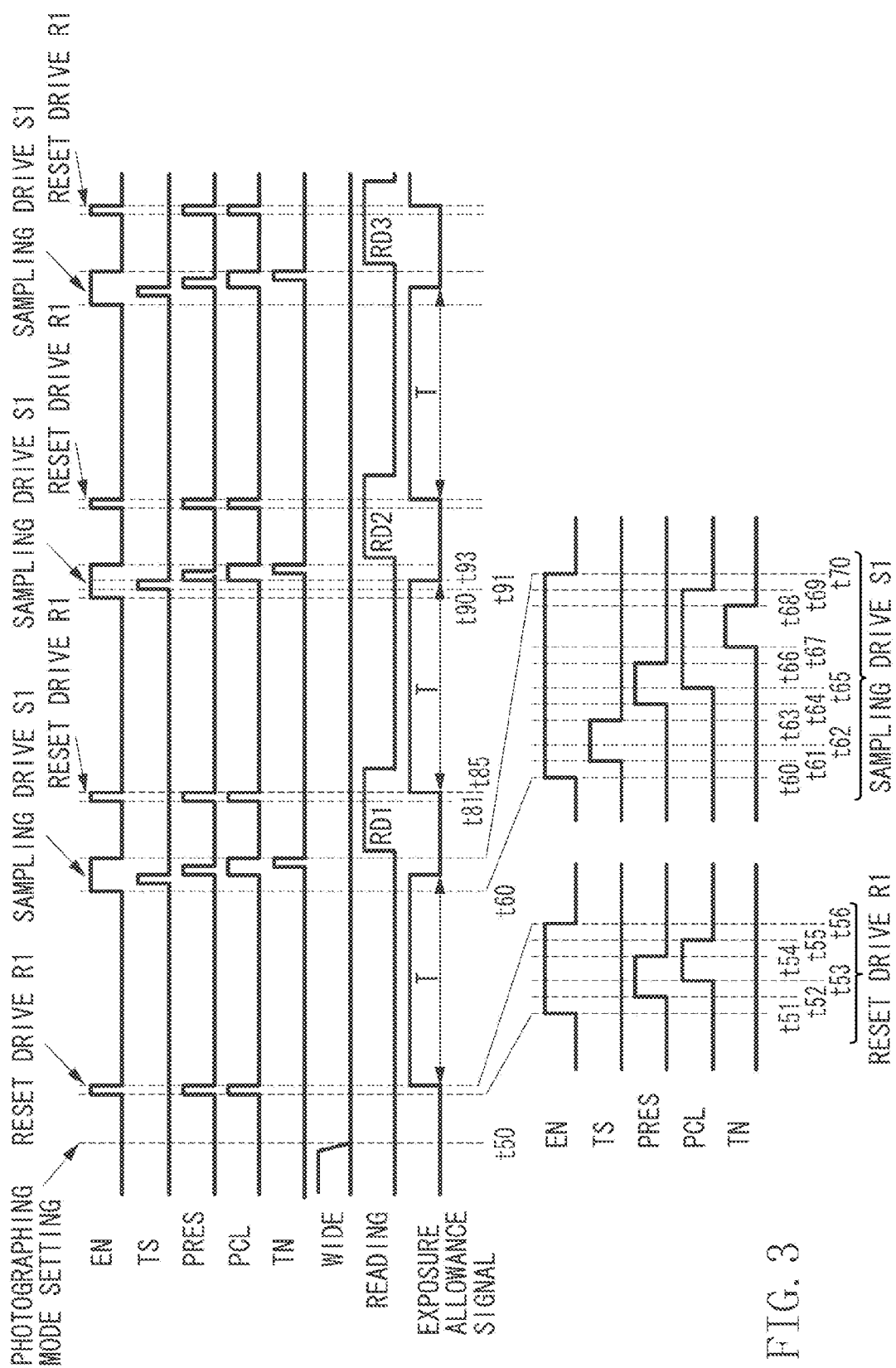
FIG. 3 is a timing chart illustrating drive timing of the pixel circuit illustrated in FIG. 2.

FIG. 3 is a timing chart illustrating exemplary drive timing in a moving image capturing operation that can be performed by the pixel circuit illustrated in FIG. 2 at a fixed frame rate with the limitation of an X-ray window. Hereinafter, the timing of control signals to be supplied until electric charges are sampled and held in the optical signal holding capacitor CS and the noise signal holding capacitor CN in the moving image capturing operation will be described below with reference to FIG. 3.

In the timing chart illustrated in FIG. 3, the pixel circuit sets the photographing mode at time t50 and starts a photographing drive operation at time t51. The pixel circuit starts a reset drive R1 at time t51, as described in detail below.

The reset drive R1 includes performing reset and clamp processing. First, at time t51, the pixel circuit brings the enable signal EN into a high level to activate the first pixel amplifier (M4) and the second pixel amplifier (M7). Then, at time t52, the pixel circuit brings the reset signal PRES into a high level to connect the photo diode PD to a reference voltage VRES.

Then, at time t53, the pixel circuit brings the clamp signal PCL into a high level to turn on the clamp switch (M5). At this moment, the reference voltage VCL is connected to the second pixel amplifier (M7) of the clamp capacitor (Ccl).

At time t54, the pixel circuit brings the reset signal PRES into a low level to complete the reset processing. At this moment, a reset voltage can be set for the first pixel amplifier (M4) of the clamp capacitor (Ccl).

At time t55, the pixel circuit turns off the clamp switch (M5). At this moment, an electric charge that corresponds to a difference between the reference voltage VCL and the reference voltage VRES can be stored in the clamp capacitor (Ccl). The pixel circuit terminates the clamp processing. Then, after terminating the above-described reset drive R1, at time t55, the pixel circuit starts storage processing for the photoelectric conversion region of the photo diode PD and the floating diffusion capacitor (Cfd).

More specifically, at time t56, the pixel circuit brings the enable signal EN into a low level to deactivate the first pixel amplifier (M4) and the second pixel amplifier (M7). Further, after reaching the storage state, the pixel circuit brings the exposure allowance signal 114 into the enable state to request the X-ray exposure. The above-described timing is applicable in the control of a subsequent reset drive.

The rectangular semiconductor substrates 106 having been tiled as described above perform the batch reset drive for all pixels of each image sensor, at the same timing and at the same period, to eliminate any image misregistration that may occur due to time difference in switching between image sensors or between scanning lines in a moving image capturing operation. Subsequently, a storage based on a one-shot exposure is performed and a photoelectric charge generated by the photo diode PD of each pixel circuit is stored in the capacitor (Cfd).

A reset noise (i.e., a kTC noise) generates in the photoelectric conversion region when the reference voltage VRES is applied to the photo diode PD in a duration between time t52 to time t54 of the reset drive R1. However, the reset noise can be removed by setting the reference voltage VCL to the second pixel amplifier (M7) of the clamp capacitor (Ccl) of the clamp circuit.

A sampling drive S1 starts at time t60, as described in detail below.

At time t60, the pixel circuit brings the enable signal EN into a high level to turn on the first selection switch (M3) and the second selection switch (M6). Thus, the electric charges stored in the capacitor (Cfd) can be charge/voltage converted and output, as a voltage, to the clamp capacitor (Ccl) by the first pixel amplifier (M4) that operates as the source follower.

The output of the first pixel amplifier (M4) includes reset noises. However, the clamp circuit sets the second pixel amplifier (M7) to the reference voltage VCL in a reset operation. Therefore, an optical signal including no reset noises can be output to the second pixel amplifier (M7).

At time t61, the pixel circuit brings the signal TS into a high level to turn on the optical signal dedicated sample-hold switch (M8). At this moment, the batch transfer of the optical signal can be performed to the optical signal holding capacitor (CS) via the second pixel amplifier (M7). As the sample-hold processing has been started, at time t62, the pixel circuit brings the exposure allowance signal 114 into a disable state to stop the X-ray exposure.

At time t63, the pixel circuit brings the signal TS into a low level to turn off the optical signal dedicated sample-hold switch (M8). Thus, the optical signal can be sampled and held by the optical signal holding capacitor (CS).

At time t64, the pixel circuit brings the reset signal PRES into a high level to turn on the reset switch (M2) to reset the capacitor (Cfd) to the reference voltage VRES. Next, at time t65, the pixel circuit brings the clamp signal PCL into a high level. Thus, an electric charge, in which a reset noise component is superimposed on the difference voltage between the reference voltage VCL and the reference voltage VRES, can be stored in the clamp capacitor (Ccl).

At time t66, the pixel circuit brings the reset signal PRES into a low level to complete the reset processing. At time t67, the pixel circuit brings the signal TN into a high level to turn on the noise signal dedicated sample-hold switch (M11). The noise signal, at the moment the reference voltage VCL has been set, can be transferred to the noise signal holding capacitor (CN).

Subsequently, at time t68, the pixel circuit brings the signal TN into a low level to turn off the noise signal dedicated sample-hold switch (M11). Thus, the noise signal can be sampled and held in the noise signal holding capacitor (CN). At time t69, the pixel circuit brings the clamp signal PCL into a low level. At time t70, the pixel circuit brings the enable signal EN into a low level to terminate the sampling drive S1. The pixel circuit performs the sampling drive S1 in a lump sum for all pixels.

The above-described timing is applicable in the control of a subsequent sampling drive. After completing the sampling drive S1, at time t81, the pixel circuit performs the reset drive R1 again to start the storage in the photo diode PD of the next frame.

The pixel circuit performs scanning of the optical signal and the noise signal stored in the optical signal holding capacitor (CS) and the noise signal holding capacitor (CN) for each pixel. When the optical signal transfer switch (M9) is turned on, the voltage of the optical signal holding capacitor (CS) can be transferred to an optical signal output line via the optical signal dedicated pixel amplifier (M10).

Further, when the noise signal transfer switch (M12) is turned on, the voltage of the noise signal holding capacitor (CN) can be transferred to a noise signal output line via the noise signal dedicated pixel amplifier (M13).

The signals transferred to the optical signal output line and the noise signal output line are supplied to a differential input amplifier (not illustrated) to which the optical signal output line and the noise signal output line are connected. The differential input amplifier performs subtraction processing on the signals received via the optical signal output line and the noise signal output line, respectively, to remove thermal noises, 1/f noises, temperature differences, and fixed pattern noises (FPN) derived from process variations that may be generated in the pixel amplifiers.

The period during which the reading from the sensor is feasible is a duration from time t68 (i.e., the sample-hold completion timing) to time t91 (i.e., the sample-hold restart timing of a photoelectric charge signal for the next frame in the optical signal holding capacitor (CS) and the noise signal holding capacitor (CN)). The pixel circuit performs pixel reading processing RD1 after completing the sampling drive S1. More specifically, the pixel circuit performs the reading processing immediately after completing the sample-hold processing so that the delay in image display can be reduced as much as possible.

In the pixel circuit illustrated in FIG. 2, the storage start timing of the photo diode PD is time t55 and time t69 illustrated in FIG. 3, i.e., the time when the signal PCL turns into a low level after completing the reset processing to complete the clamp. Further, the storage completion timing is time t63, i.e., the time when the signal TS turns into a low level to sample and hold the optical signal.

As described above, the storage time can be limited by inserting the reset drive R1 or the sampling drive S1 (to be performed to start the storage time) between the sampling drive S1 and the sampling drive S1 (to be performed to sample and hold the optical signal and the noise signal).

In FIG. 3, the reset drive R1 that starts at time t81 is inserted between the sampling drive S1 that starts at time t60 and the sampling drive S1 that starts at time t90. Thus, the X-ray window (i.e., the substantial storage time) can be limited to a period T between time t85 to time t93.

Figure 4:
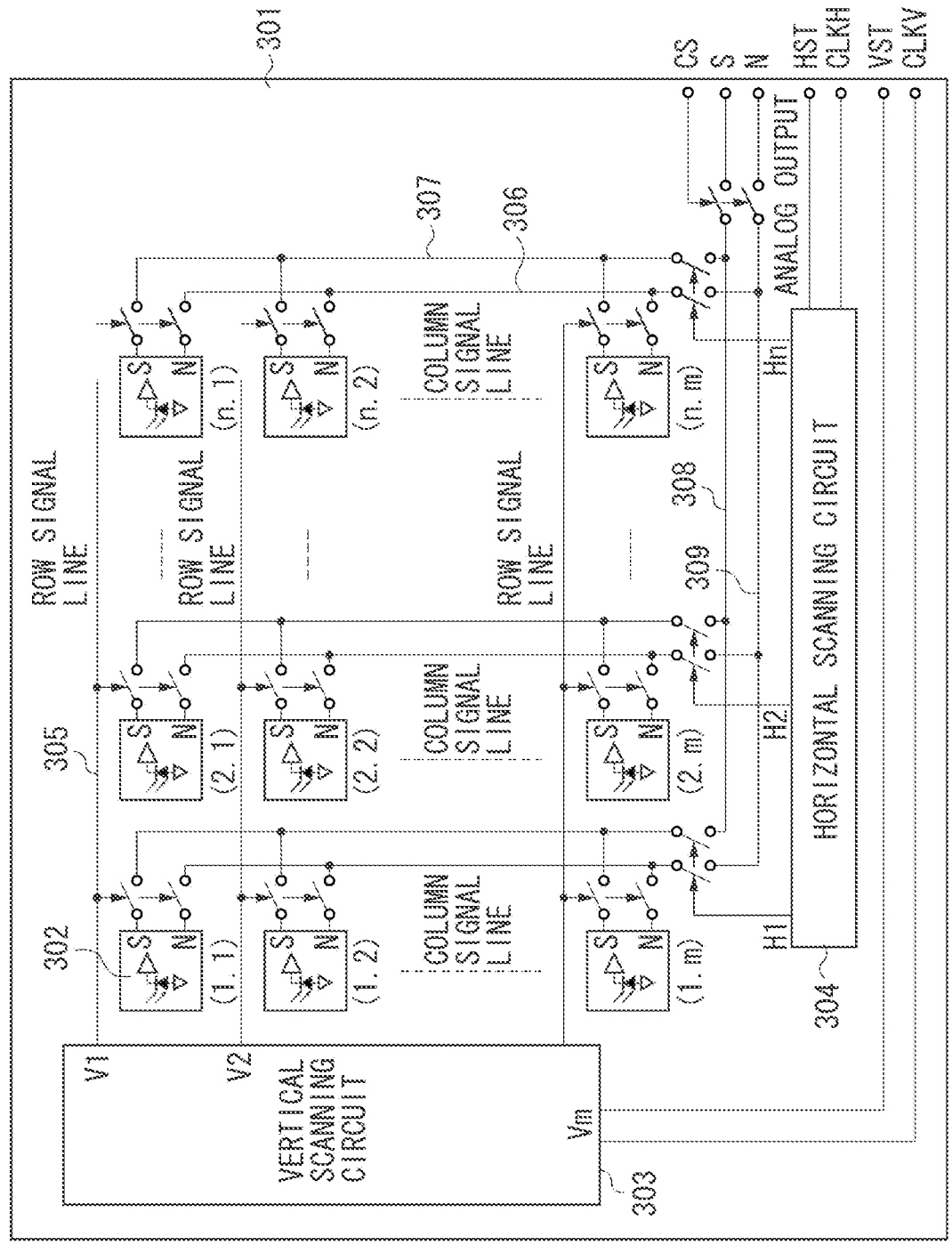
FIG. 4 illustrates a configuration example of a rectangular semiconductor substrate according to the present exemplary embodiment.

FIG. 4 schematically illustrates an example of an internal structure of the rectangular semiconductor substrate according to the present exemplary embodiment.

A rectangular semiconductor substrate 301 illustrated in FIG. 4 includes a chip select signal terminal CS, an optical signal output terminal S, a noise signal output terminal N, a vertical scanning start signal terminal VST, a vertical scanning clock terminal CLKV, a horizontal scanning start signal terminal HST, and a horizontal scanning clock terminal CLKH.

A vertical scanning circuit 303 can select a group of a plurality of pixels arranged in the horizontal direction and sequentially scan the pixel group in the vertical direction (i.e., sub scanning direction) in synchronization with the vertical scanning clock CLKV. A horizontal scanning circuit 304 can sequentially select, pixel by pixel, column signal lines of the pixel group arranged in the horizontal direction (i.e., main scanning direction), which has been selected by the vertical scanning circuit 303, in synchronization with the horizontal scanning clock CLKH.

A pixel circuit 302 is the pixel circuit illustrated in FIG. 2. When a row signal line 305 (i.e., an output line of the vertical scanning circuit 303) is in an enable state, an optical signal voltage signal S and a noise voltage signal N having been sampled and held can be output to column signal lines 307 and 306, respectively.

The horizontal scanning circuit 304 sequentially selects the voltage signals having been output to the column signal lines 306 and 307. Thus, voltage signals of respective pixels can be sequentially output to analog output lines 308 and 309.

As described above, the rectangular semiconductor substrate 301 performs an XY address switching operation using the vertical scanning circuit 303 and the horizontal scanning circuit 304 to perform pixel selection. Then, the voltage signals of the optical signal S and the noise signal N of each pixel, which have been amplified by the transistor, from the selected pixel can be output to the analog output terminals S and N via the column signal lines 306 and 307 and the analog output lines 308 and 309.

The chip select signal terminal CS is an input terminal of a chip select signal. When the chip select signal is in a high level, an optical voltage signal S and a noise voltage signal N of the image sensor that reflect internal scanning can be output via the analog output terminals S and N.

The output switching analog switches following the sample-hold circuits that relate to the optical signal and the noise signal, the column signal lines 306 and 307, and the switching transistors that switch the column signal lines according to an output of the horizontal scanning circuit 304 cooperatively constitute a reading and scanning transmission circuit.

The vertical scanning clock terminal CLKV is an input terminal of the clock to be supplied to the vertical scanning circuit 303. The vertical scanning start signal terminal VST is an input terminal of a start signal to be supplied to the vertical scanning circuit 303. The row selection signal can be sequentially enabled in order of V1, V2, . . . , and Vm when the vertical scanning clock CLKV is input after the vertical scanning start signal VST is brought into a high level.

If the vertical scanning starts, the vertical scanning start signal VST is brought into a low level. The horizontal scanning clock terminal CLKH is an input terminal of the clock to be supplied to the horizontal scanning circuit 304. The horizontal scanning start signal terminal HST is an input terminal of a start signal to be supplied to the horizontal scanning circuit 304.

The column selection signal can be sequentially enabled in order of H1, H2, . . . , and Hn when the horizontal scanning clock CLKH is input after the horizontal scanning start signal HST is brought into a high level. If the horizontal scanning starts, the horizontal scanning start signal HST is brought into a low level.

If the output of the row signal line V1 of the vertical scanning circuit 303 is brought into an enable state, a horizontally extending group of pixels (1, 1) to (n, 1) connected to the row signal line V1 is selected. The optical voltage signal S and the noise voltage signal N can be output from each pixel of the horizontally extending pixel group to the column signal lines 307 and 306, respectively.

The optical voltage signal S and the noise voltage signal N of a horizontally extending row can be sequentially output to the analog output terminals S and N via the analog output lines 308 and 309 by sequentially switching the enable state of the column selection signal of the horizontal scanning circuit 304 in order of H1, H2, . . . , and Hn. The pixel outputs of all pixels can be obtained by performing similar horizontal scanning for the remaining row signal lines V2 to Vm.

Figure 5:
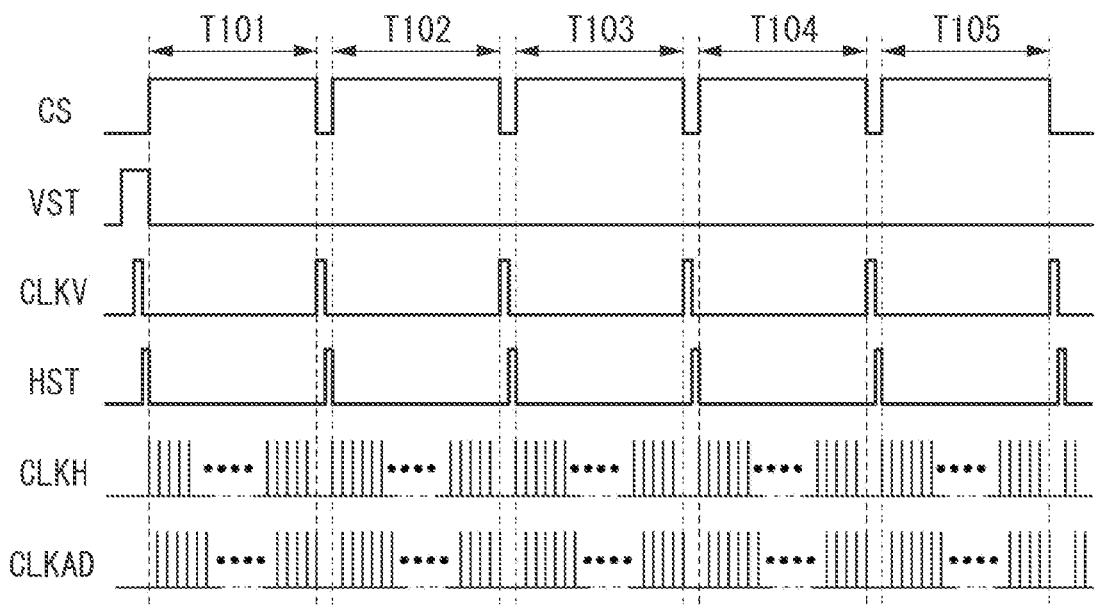
FIG. 5 illustrates a timing chart where pixel data of the rectangular semiconductor substrate is read.

FIG. 5 illustrates an exemplary timing chart where a pixel data of the rectangular semiconductor substrate is read. In FIG. 5, the timing chart illustrates reading of the pixel data of the rectangular semiconductor substrate, while one vertical scanning operation and one horizontal scanning operation are performed.

In FIG. 5, a signal CS is a chip select signal that controls the output of an analog signal of the rectangular semiconductor substrate. When the signal CS is a high-level signal, the analog output becomes effective and can be output to the next-stage amplifier 107.

If the vertical scanning clock CLKV rises in a state where the vertical scanning start signal VST is in a high level, the row signal line V1 of the vertical scanning circuit 303 illustrated in FIG. 4 becomes enabled. Then, the outputs of respective pixels (1, 1) to (n, 1) of the pixel group selected by the row signal line V1 become effective. The optical voltage signal S and the noise voltage signal N of respective pixels (1, 1) to (n, 1) of the pixel group can be output to the column signal lines.

Subsequently, if the horizontal scanning clock CLKH rises in a state where the horizontal scanning start signal HST is in a high level, the column selection signal H1 of the horizontal scanning circuit 304 becomes enabled. The column selection signal of the horizontal scanning circuit 304 is sequentially enabled in order of H2, . . . , and Hn in synchronization with the rise of the horizontal scanning clock CLKH to select the pixels (1, 1) to (n, 1) successively. Thus, the scanning of the pixel group extending in the horizontal direction on the rectangular semiconductor substrate, which has been selected by the chip select signal CS, terminates. The pixel outputs of all pixels can be obtained by performing the horizontal scanning similarly for the pixel group connected to each of the remaining row signal lines V2 to Vm.

For example, in FIG. 5, reading of signals from the pixels (1, 1) to (n, 1) belonging to the pixel group connected to the row signal line V1 can be performed in a period T101 and reading of signals from the pixels (1, 2) to (n, 2) belonging to the pixel group connected to the row signal line V2 can be performed in a period T102.

Similarly, reading of signals from the pixels of the pixel group connected to the row signal line V3 can be performed in a period T103 and reading of signals from the pixels of the pixel group connected to the row signal line V4 can be performed in a period T104. Further, reading of signals from the pixels of the pixel group connected to the row signal line V5 can be performed in a period T105. The A/D converter 108 performs A/D conversion processing based on a clock CLKAD in synchronization with the horizontal scanning clock CLKH.

Figure 6:
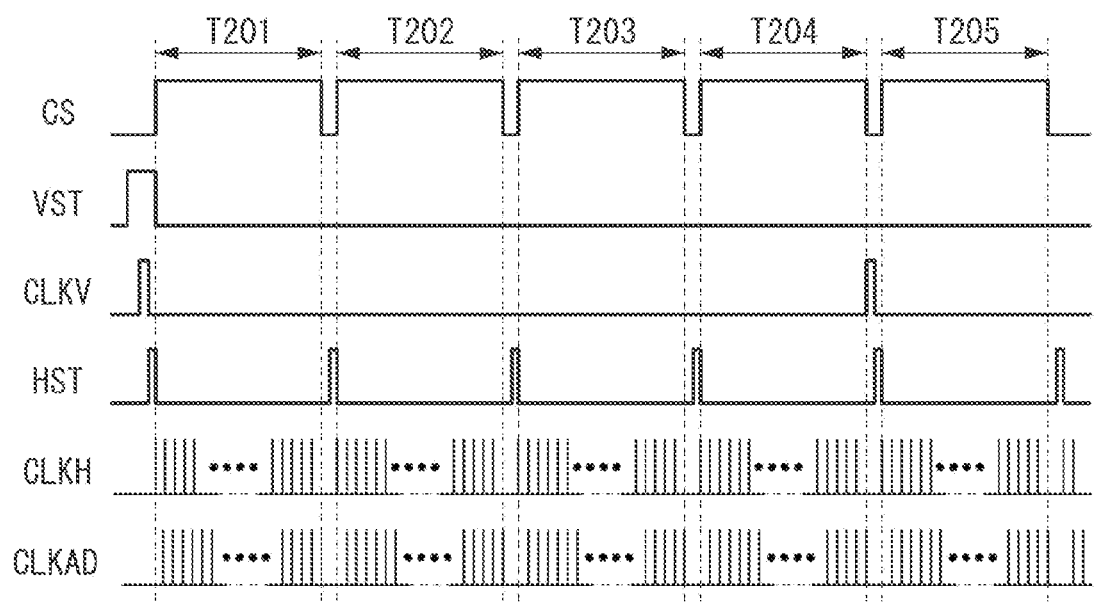
FIG. 6 illustrates a timing chart where pixel data of the rectangular semiconductor substrate is read.

FIG. 6 illustrates a timing chart where the horizontal scanning is performed four times for each row and the vertical scanning is performed once to read all pixel data on the rectangular semiconductor substrate four times.

If the vertical scanning clock CLKV rises in a state where the chip select signal CS is brought into a high level and the vertical scanning start signal VST is in a high level, the row signal line V1 of the vertical scanning circuit 303 illustrated in FIG. 4 becomes enabled.

Subsequently, the horizontal scanning clock CLKH rises in a state where the horizontal scanning start signal HST is in a high level. The column selection signal of the horizontal scanning circuit 304 is sequentially enabled in order of H1, H2, ..., and Hn. Thus, the scanning of the pixel group extending in the horizontal direction terminates.

Subsequently, the chip select signal CS is again brought into a high level, while the vertical scanning clock CLKV does not switch the row signal line of the vertical scanning circuit 303. In this state, the horizontal scanning is similarly repeated for the pixels connected to the row signal line V1. The above-described operations are repeated two more times. Thus, in a state where the row signal line V1 of the vertical scanning circuit 303 illustrated in FIG. 4 is enabled, it is feasible to perform the scanning of the pixel group extending in the horizontal direction four times.

For example, in FIG. 6, the first reading operation is performed in a period T201 to read the signals from the pixels (1, 1) to (n, 1) belonging to the pixel group connected to the row signal line V1. The second reading operation is performed in a period T202. Further, the third reading operation is performed in a period T203. The fourth reading operation is performed in a period T204.

Subsequently, the vertical scanning clock CLKV sequentially switches the enable state of the row signal line of the vertical scanning circuit 303. The horizontal scanning is similarly performed four times for each row, to complete the processing for the pixel group connected to each of the remaining row signal lines V2 to Vm. Thus, the signals of all pixels provided on the rectangular semiconductor substrate can be read four times while the vertical scanning is performed once.

For example, in FIG. 6, the reading operation to be performed in a period T205 is the first reading operation for the pixels (1, 2) to (n, 2) belonging to the pixel group connected to the row signal line V2.

The clock period of the vertical scanning clock CLKV is, for example, 1 μsec. Therefore, in a case where the reading operation is performed four times for all pixels provided on the rectangular semiconductor substrate, it takes 4 m (μsec) to complete the vertical scanning processing according to the reading method illustrated in FIG. 5 because the vertical scanning is performed four times for each of the first to m-th rows.

However, the reading method illustrated in FIG. 6 requires one scanning operation in the vertical direction. Therefore, the time required for the vertical scanning is 1 m (μsec). More specifically, the reading method illustrated in FIG. 6 can speedily complete the reading processing compared to the reading method illustrated in FIG. 5. The completion timing is 3 m (μsec) earlier. For example, a pixel clock of 20 MHz is usable to perform the horizontal scanning. In this case, the time required to complete the horizontal scanning for the first column to the n-th column is 0.05 n (μsec).

Figure 7:
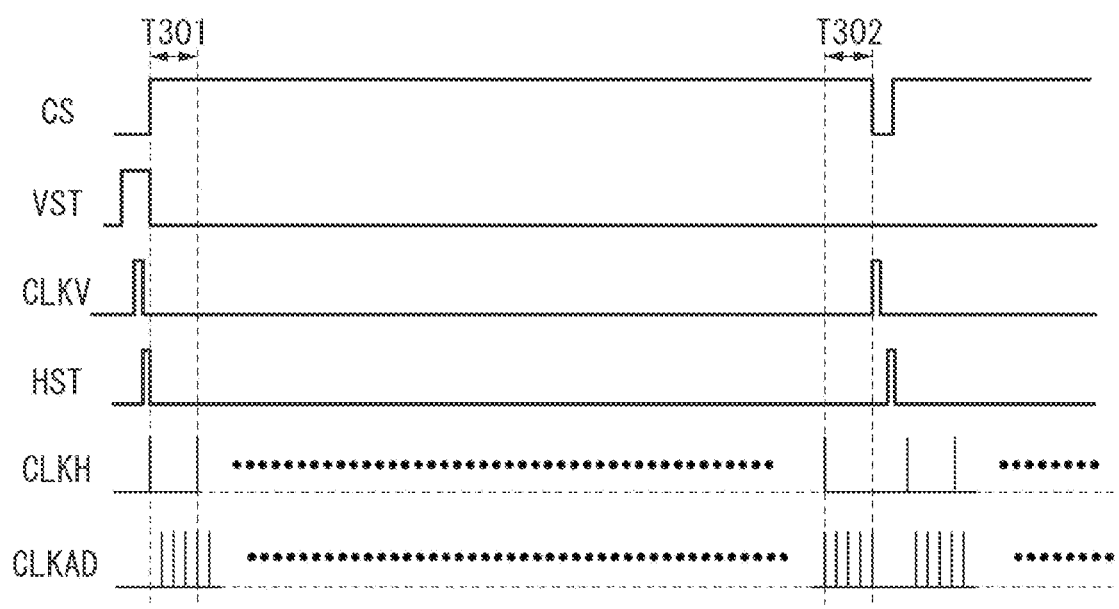
FIG. 7 illustrates a timing chart where pixel data of the rectangular semiconductor substrate is read.

Further, in a state where the row signal line V1 of the vertical scanning circuit 303 is enabled, and when the pixel (1, 1) is selected by enabling the column selection signal H1 of the horizontal scanning circuit 304, it is feasible to read the pixel data four times consecutively. FIG. 7 is a timing chart illustrating an example of the reading method. If the vertical scanning clock CLKV rises in a state where the chip select signal CS is brought into a high level when the vertical scanning start signal VST is in a high level, the row signal line V1 of the vertical scanning circuit 303 illustrated in FIG. 4 becomes enabled.

Subsequently, if the horizontal scanning clock CLKH rises in a state where the horizontal scanning start signal HST is in a high level, the column selection signal H1 of the horizontal scanning circuit 304 is enabled. In this state, the clock CLKAD rises four times to read the signal from the pixel (1, 1) four times consecutively (see period T301).

Hereinafter, the four consecutive reading operations can be performed for each pixel, while sequentially switching the column selection signal of the horizontal scanning circuit 304 and the row signal line of the vertical scanning circuit 303 using the horizontal scanning clock CLKH and the vertical scanning clock CLKV. Thus, the four times reading operation for each of all pixels provided on the rectangular semiconductor substrate can be performed while one vertical scanning operation and one horizontal scanning operation are performed.

However, in a case where the reading processing is repeated plural times for each pixel, it is difficult to remove low-frequency noise components even when averaging processing is performed for each pixel. Therefore, in the present exemplary embodiment, it is desired to perform a plurality of non-destructive reading operations using the reading method illustrated in FIG. 6, rather than using the reading method illustrated in FIG. 7. In the following description, it is presumed that the reading method illustrated in FIG. 6 is employed to perform a plurality of non-destructive reading operations.

Figure 8A:
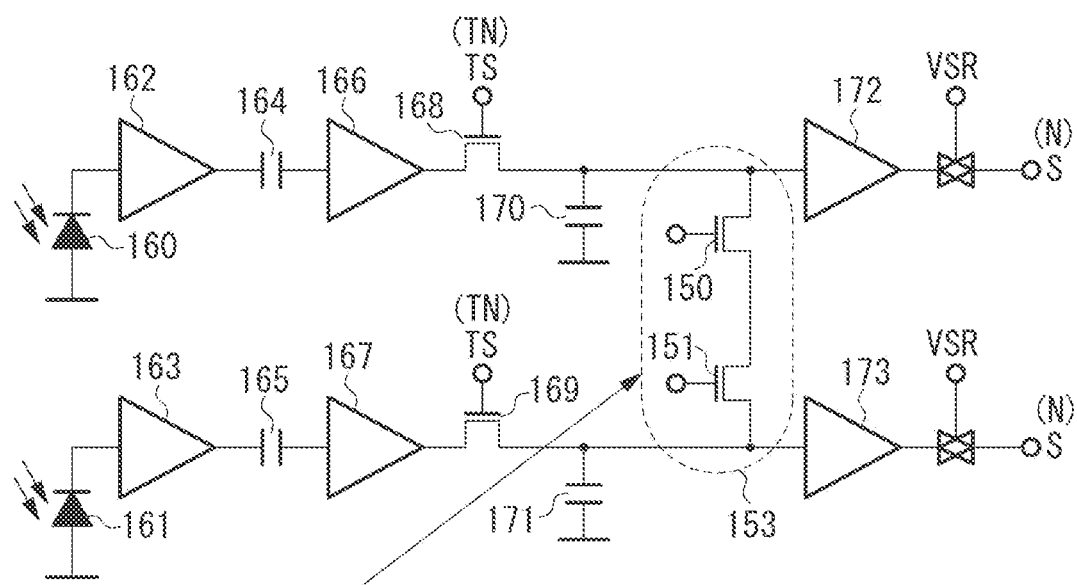
FIGS. 8A and 8B illustrate an example of a pixel addition circuit included in the rectangular semiconductor substrate according to the present exemplary embodiment.
Figure 8B:
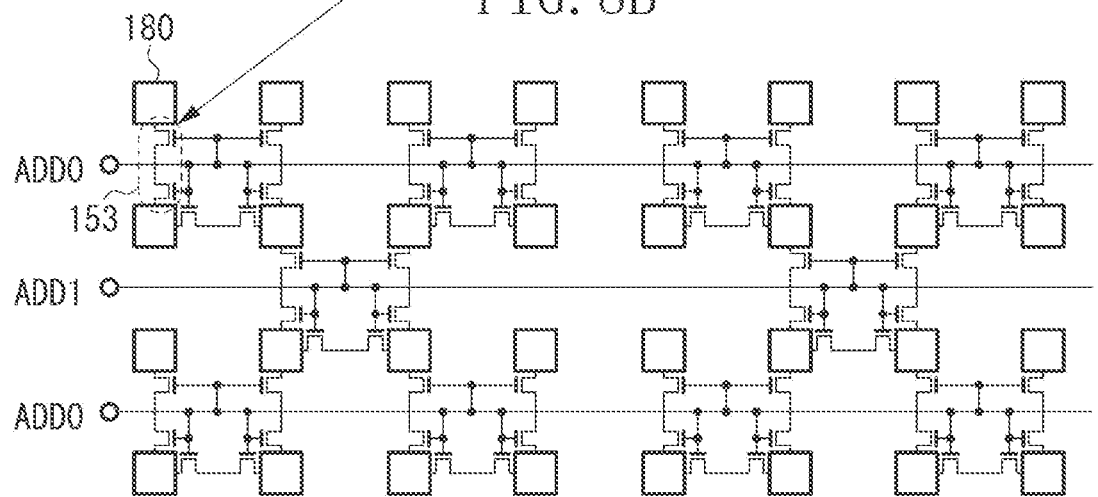

FIGS. 8A and 8B illustrate an exemplary circuit configuration of a pixel addition circuit included in the rectangular semiconductor substrate according to the present exemplary embodiment.

FIG. 8A illustrates an example of a circuit including a pixel addition circuit that is inserted in a circuit that includes two simplified pixel circuits each being illustrated in FIG. 2.

An actual circuit includes pixel addition circuits that are provided for the optical signal and the noise signal, respectively. However, to simplify the description, FIGS. 8A and 8B illustrate only one of the sample-hold circuits for the optical signal and the noise signal.

Respective circuits include photo diodes 160 and 161 that correspond to the photo diode PD illustrated in FIG. 2. Respective circuits further include amplification MOS transistors (i.e., pixel amplifiers) 162, 163, 166, 167, 172, and 173 that are operable as source followers. The amplification MOS transistors 162 and 163 correspond to the first pixel amplifier (M4) illustrated in FIG. 2. The amplification MOS transistors 166 and 167 correspond to the second pixel amplifier (M7) illustrated in FIG. 2. The amplification MOS transistors 172 and 173 correspond to the optical signal dedicated pixel amplifier (M10) or the noise signal dedicated pixel amplifier (M13) illustrated in FIG. 2.

Respective circuits further include clamp capacitors 164 and 165 that correspond to the clamp capacitor (Ccl) illustrated in FIG. 2. Two sample MOS transistors (i.e., sample-hold switches) 168 and 169 constitute an optical signal storage sample-hold circuit or a noise signal storage sample-hold circuit. The sample MOS transistors 168 and 169 correspond to the optical signal dedicated sample-hold switch (M8) or the noise signal dedicated sample-hold switch (M11) illustrated in FIG. 2.

Respective circuits further include an optical signal dedicated holding capacitor or a noise signal dedicated holding capacitor (see 170 or 171), which corresponds to the optical signal holding capacitor (CS) or the noise signal holding capacitor (CN) illustrated in FIG. 2. Two addition dedicated MOS transistors (i.e., addition switches) 150 and 151 cooperatively constitute a pixel addition circuit.

FIG. 8B illustrates an exemplary connection of a pixel circuit 180 and a pixel addition circuit 153 that cooperatively constitute one pixel of the rectangular semiconductor substrate. A circuit portion 153 indicated by a dotted line in FIG. 8A corresponds to the circuit portion 153 indicated by a dotted line in FIG. 8B.

As illustrated in FIG. 8B, the pixel addition can be realized by connecting the optical signal (or noise signal) dedicated holding capacitors of neighboring pixels. Thus, the number of pixels to be scanned can be reduced without discarding pixel information. The signal reading processing can be performed at a high frame rate.

In FIG. 8B, when a signal ADD0 is brought into a high level and a signal ADD1 is brought into a low level, an addition of 2×2 pixels can be realized. Further, when the signal ADD0 is brought into a high level and the signal ADD1 is brought into a high level, an addition of 4×4 pixels can be realized. Further, the above-described pixel addition circuit can be combined with the sensitivity selection switch (M1) illustrated in FIG. 2 to realize the switching of sensitivity.

For example, if addition processing or averaging processing is performed on pixel information of 2×2 pixels, an image can be speedily acquired by performing a simple addition reading of analog signals illustrated in FIGS. 8A and 8B in a case where processing for reducing pixel information of one pixel is performed.

However, in a case where at least one of 2×2 pixels is defective, the pixels having been subjected to the addition processing are regarded as defective pixels. More specifically, in this case, the image having been subjected to reduction processing greatly deteriorates due to the presence of the defective pixels. Hence, the processing according to the present exemplary embodiment includes performing the above-described reduction processing without including any pixel information of defective pixels to prevent the image having been subjected to the reduction processing from deteriorating.

The processing according to the present exemplary embodiment includes acquiring a digital value that is obtainable by performing A/D conversion on the pixel information and then selecting pixel information of normal pixels based on defective pixel positional information. The processing according to the present exemplary embodiment further includes performing the addition processing (i.e., digital binning processing) using the selected pixel information to obtain a pixel addition result that does not include any defective pixels.

Alternatively, the processing according to the present exemplary embodiment can include acquiring a digital value that represents image data having been subjected to analog signal based pixel addition processing, subsequently selecting pixel information of normal pixels based on defective pixel positional information, and finally performing the digital binning processing using the selected pixel information. In this case, it is feasible to reduce the number of pixels to be scanned so that the signal reading processing can be performed at a high frame rate and a pixel addition result without defective pixels can be obtained.

In a case where an inherently defective pixel is subjected to the analog signal based pixel addition processing and when the values of neighboring pixels are averaged, the defectiveness of the pixel may be eliminated. On the other hand, a new defective pixel may be generated due to a malfunction of the pixel addition circuit illustrated in FIGS. 8A and 8B. Further, the defective pixel is variable depending on the sensitivity of a pixel circuit. Therefore, it is necessary to prepare defective pixel positional information that corresponds to all photographing modes (e.g., image size and sensitivity) according to which a solid-state imaging apparatus can perform a photographing operation.

Further, a reading signal obtained by an image sensor includes random noises. The sensor employed in the present exemplary embodiment is a solid-state image sensor that can perform a non-destructive reading operation. Thus, it is feasible to reduce randomly generating noises and improve the signal to noise ratio (S/N) by reading a signal stored during a single exposure plural times and obtaining an average value.

FIG. 9 illustrates a configuration example of the flat panel sensor 105 and the photographing control unit 109 according to the present exemplary embodiment. In FIG. 9, a functional block similar to that in the block diagram illustrated in FIG. 1 is denoted by the same reference numeral and the description thereof is not repeated.

The photographing control unit 109 includes a driving circuit 127, a non-destructive multiple reading averaging circuit 121, a digital binning circuit 122, a defective information storage buffer 128, and an image pre-transfer buffer 123. The driving circuit 127 can perform a drive control and a photographing mode control for the flat panel sensor 105.

The non-destructive multiple reading averaging circuit 121 can perform the averaging processing on the pixel (i.e., photoelectric conversion element) signals obtained through a plurality of non-destructive reading operations. The digital binning circuit 122 can perform the digital binning processing for spatially binning added signals.

The defective information storage buffer 128 can temporarily store defective pixel positional information to be used in the digital binning processing. The photographing control unit 109 can output image data based on the signal having been subjected to the binning processing. The defective pixel positional information stored in the defective information storage buffer 128 is, for example, changeable according to a setting state of the imaging apparatus.

The image pre-transfer buffer 123 can temporarily store an image to be transferred to the system control apparatus 101. In the present exemplary embodiment, the photographing control unit 109 can be realized by a semiconductor apparatus (e.g., Field Programmable Gate Array (FPGA)) whose circuit configuration is programmable. The non-destructive multiple reading averaging circuit 121 and the digital binning circuit 122 are disposed on the same semiconductor apparatus (e.g., FPGA).

Further, it is useful to provide a plurality of semiconductor apparatuses (e.g., FPGAs) on which the non-destructive multiple reading averaging circuit 121 and the digital binning circuit 122 are provided. In this case, respective semiconductor apparatuses can perform processing for mutually different partial regions of an imaging region of the flat panel sensor 105. For example, it is useful to provide a plurality of semiconductor apparatuses (e.g., FPGAs), on which the non-destructive multiple reading averaging circuit 121 and the digital binning circuit 122 are provided, for each rectangular semiconductor substrate 106 of the flat panel sensor 105, to execute the processing.

The non-destructive multiple reading averaging circuit 121 includes a non-destructive multiple reading averaging processing buffer 129. The digital binning circuit 122 includes a digital binning processing buffer 130.

In FIG. 9, a selection circuit 131 can select the presence of processing to be performed by the non-destructive multiple reading averaging circuit 121. A selection circuit 132 can select the presence of processing to be performed by the digital binning circuit 122.

The defective pixel positional information to be used in the digital binning processing is, for example, stored in a memory 124 (e.g., a double-data-rate (DDR) dynamic random access memory) that is provided outside the photographing control unit 109. The defective pixel positional information is, for example, a plurality of pieces of information that corresponds to various photographing modes (e.g., image size and sensitivity, in other words, binning processing and gain), which is stored in the memory 124. The reading of defective pixel positional information from the memory 124 to the defective information storage buffer 128 can be performed, for example, when a photographing mode is set or when the power source is turned on.

The flat panel sensor 105 includes a pixel addition circuit 120, as an analog binning unit. The pixel addition circuit 120 corresponds to the pixel addition circuit illustrated in FIGS. 8A and 8B. A central processing unit (CPU) 126 is operable as a control unit configured to control the photographing control unit 109. A program memory 125 stores a program required to perform the above-described control.

The processing according to the present exemplary embodiment includes a combined averaging and digital binning processing applied to pixel signals obtained through a plurality of non-destructive reading operations. In the present exemplary embodiment, it is presumed that the pixel addition circuit 120 does not perform the binning processing and the number of non-destructive reading operations to be performed for one pixel is four times, and is further presumed that a pixel group to be subjected to the digital binning processing is 2×2 pixels.

As illustrated in FIG. 6, the processing according to the present exemplary embodiment includes repetitively performing the horizontal scanning operation four times for each row of pixel data having been sampled, and reading all of the pixel data from the rectangular semiconductor substrate four times while performing the vertical scanning operation once. The pixel data having been read is successively subjected to the A/D conversion to be performed by the A/D converter 108 and supplied to the non-destructive multiple reading averaging circuit 121 via the selection circuit 131.

In the present exemplary embodiment, pixel data L1 of a pixel group extending in the horizontal direction can be read and A/D converted in the first horizontal scanning operation when the row signal line V1 is enabled by the vertical scanning circuit 303. Then, pixel data L2 of a pixel group extending in the horizontal direction can be read and A/D converted in the second horizontal scanning operation. Similarly, pixel data L3 of a pixel group extending in the horizontal direction can be read and A/D converted in the third horizontal scanning operation. Then, pixel data L4 of a pixel group extending in the horizontal direction can be read and A/D converted in the fourth horizontal scanning operation.

Further, pixel data L5 of a pixel group extending in the horizontal direction can be read and A/D converted in the first horizontal scanning operation when the row signal line V2 is enabled by the vertical scanning circuit 303. Then, pixel data L6 of a pixel group extending in the horizontal direction can be read and A/D converted in the second horizontal scanning operation. Similarly, pixel data L7 of a pixel group extending in the horizontal direction can be read and A/D converted in the third horizontal scanning operation. Then, pixel data L8 of a pixel group extending in the horizontal direction can be read and A/D converted in the fourth horizontal scanning operation.

The pixel data L1 having been input in the non-destructive multiple reading averaging circuit 121 can be stored in the non-destructive multiple reading averaging processing buffer 129. Then, the non-destructive multiple reading averaging circuit 121 adds the subsequently input pixel data L2 to the pixel data L1 stored in the buffer 129 for each pixel. The addition result, i.e., pixel data (L1+L2), can be stored in the buffer 129.

Further, the non-destructive multiple reading averaging circuit 121 adds the subsequently input pixel data L3 to the pixel data (L1+L2) stored in the buffer 129 for each pixel. The addition result, i.e., pixel data (L1+L2+L3), can be stored in the buffer 129.

Subsequently, the non-destructive multiple reading averaging circuit 121 adds the input pixel data L4 to the pixel data (L1+L2+L3) stored in the buffer 129 for each pixel.

Then, the non-destructive multiple reading averaging circuit 121 divides the addition result, i.e., pixel data (L1+L2+L3+L4), by 4 for each pixel to obtain an averaged pixel data D1=((L1+L2+L3+L4)/4) of the pixel group extending in the horizontal direction.

Then, the pixel data D1 is input to the digital binning circuit 122. Similar averaging processing is performed to obtain averaged pixel data D2=((L5+L6+L7+L8)/4). The pixel data D2 is also input to the digital binning circuit 122. The pixel data D1, . . . , and Dn, having been obtained by the non-destructive multiple reading averaging circuit 121, are sequentially input to the digital binning circuit 122.

To perform the above-described processing, it is desired to constitute the buffer 129 of the non-destructive multiple reading averaging circuit 121 by a line buffer having a sufficient capacity capable of storing pixel data of one row of the read image size.

The pixel data D1 of the pixel group extending in the horizontal direction having been input to the digital binning circuit 122 is composed of a total of n pixels having addresses (1, 1) to (n, 1). The digital binning circuit 122 performs the addition processing, using the input pixel data, to obtain a set of pixels to be subjected to the binning processing performed in the horizontal direction. In this case, the digital binning circuit 122 performs the addition processing by selecting only the pixel information of normal pixels based on the defective pixel positional information stored in the defective information storage buffer 128.

In the present exemplary embodiment, each pixel group to be processed is composed of 2×2 pixels. Therefore, the digital binning circuit 122 repeats an addition of two pixels. More specifically, the digital binning circuit 122 obtains an addition of (1, 1) and (2, 1), an addition of (3, 1) and (4, 1), . . . , and an addition of (n−1, 1) and (n, 1) from the pixel data D1. Then, pixel data D1' including a total of (n/2) pixels is stored in the digital binning processing buffer 130. Similarly, the digital binning circuit 122 obtains an addition of (1, 2) and (2, 2), . . . , and an addition of (n−1, 2) and (n, 2) from the pixel data D2.

Then, the digital binning circuit 122 adds the obtained addition result (i.e., pixel data D2') to the pixel data D1' stored in the buffer 130 for each pixel to obtain an average based on the number of effective pixels. As a result, for example, it is feasible to obtain a pixel addition result that does not include any defective pixels by averaging the pixel information of 2×2 pixels composed of (1, 1) and (2, 1), and, (1, 2) and (2, 2) pixels. To perform the above-described processing, it is desired to constitute the buffer 130 of the digital binning circuit 122 by a line buffer that has the capability of storing pixel data of one row of the image size having been subjected to the digital binning processing.

The processing according to the present exemplary embodiment includes reading defective pixel positional information of a pixel portion to be subjected to the digital binning processing from the memory 124 each time the digital binning processing is performed and storing the read defective pixel positional information in the defective information storage buffer 128 of the photographing control unit 109.

Figure 10A:
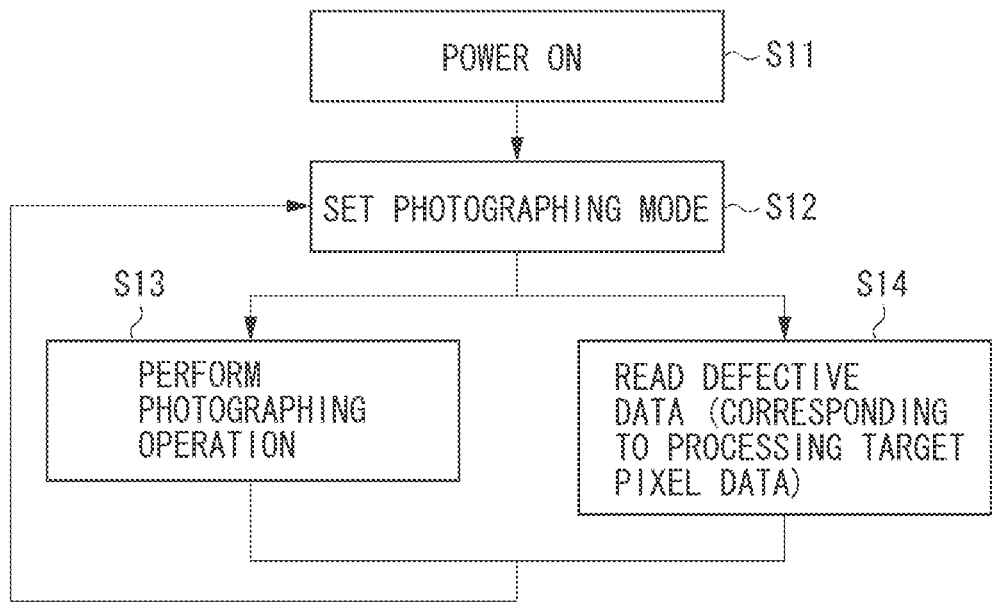
FIGS. 10A, 10B, and 10C illustrate flowcharts of processing that can be performed according to the present exemplary embodiment.

FIG. 10A illustrates a flowchart of processing according to the present exemplary embodiment.

In step S11, the power source of the imaging apparatus is turned on. Then, in step S12, a photographing mode is set. Subsequently, in step S13, a photographing operation including the digital binning processing is performed. Simultaneously, in step S14, defective pixel positional information that is preferable for the photographing mode is read from the memory 124. The read defective pixel positional information is stored in the defective information storage buffer 128 of the photographing control unit 109.

Performing the above-described processing for reading defective pixel positional information from the memory 124 in parallel with the digital binning processing is useful to realize a circuit that can minimize the capacitance of the defective information storage buffer 128. Even when the photographing control unit 109 accesses the memory 124, which is externally provided, while performing the digital binning processing, there is not any adverse influence on the processing speed of the circuit because the digital binning processing according to the present exemplary embodiment is performed once for each frame.

The image data having been subjected to the digital binning processing of the digital binning circuit 122 is sequentially input to the image pre-transfer buffer 123. The image data stored in the image pre-transfer buffer 123 is subsequently transferred to the image processing unit of the system control apparatus 101.

The image pre-transfer buffer 123 can be replaced by an external memory (e.g., DDR) provided outside the photographing control unit 109. For example, the above-described memory is the memory 124, the memory 124 simultaneously performs reading of the defective pixel positional information and a writing/reading access of an image to be transferred. However, in the present exemplary embodiment, the digital binning processing is performed once for one frame. Therefore, the processing speed of the circuit can be maintained effectively.

The processing according to the present exemplary embodiment includes horizontally scanning sampled pixel data four times for each row and averaging the scanned results of each row to further perform the digital binning processing. Therefore, it is feasible to reduce random noises without increasing the reading time.

Further, it is feasible to prevent the image quality from deteriorating due to the presence of any defective pixels because the digital binning processing is performed using only the pixel information of normal pixels with reference to defective pixel positional information. Further, it is feasible to reduce the circuit scale because a minimum necessary line buffer is usable as a buffer of each circuit in performing the above-described processing according to the present exemplary embodiment.

Further, compared to the method characterized by repetitively reading one frame four times, the method for reading each row consecutively by performing the horizontal scanning operation four times is useful to increase the frame rate because the reading time can be reduced.

Further, the processing according to the present exemplary embodiment includes performing the digital binning processing once for one frame. Therefore, the processing speed of the circuit can be increased effectively without increasing the number of times the defective pixel positional information is read out from the memory 124 (i.e., the number of times the memory is accessed). The above-described effect can be further enhanced if the memory that stores the defective pixel positional information is a memory (e.g., DDR) provided outside the photographing control unit 109.

The number of times the pixel signal is non-destructively read out from the flat panel sensor is not limited to the above-described example. Further, the size of the matrix to be subjected to the digital binning processing is not limited to the above-described example. Therefore, any other n×n matrix (n is a natural number) is usable. Further, it is also feasible to perform the above-described processing without reading any defective pixel positional information during the digital binning processing.

Further, the pixel addition circuit 120, the non-destructive multiple reading averaging circuit 121, and the digital binning circuit 122 are independent circuits and can be arbitrarily combined with one another. The data read out from the sensor 105 can be data acquired by the pixel addition circuit 120. It is feasible to perform the pixel addition processing and the digital binning processing in the sensor.

For example, if 2×2 digital binning processing is performed on a processing result of the binning processing performed on the 2×2 pixels by the pixel addition circuit 120, an image finally transferred to the system control apparatus 101 is a result obtained through 4×4 binning processing.

For example, in a case where the binning processing to be performed on 4×4 pixels is only the digital binning processing, the pixel addition circuit 120 reads a 1×1 image without any binning processing and the digital binning circuit 122 performs 4×4 digital binning processing. In this case, a significant processing time is required because the number of pixels to be processed in each of the A/D conversion, the averaging processing, and the digital binning processing is 1×1.

On the other hand, in a case where 2×2 digital binning processing is performed on a processing result of 2×2 binning processing with the analog signal based pixel addition processing in the sensor 105, the number of pixels to be subjected to the scanning in the sensor can be reduced. Therefore, it becomes feasible to read signals at a high frame rate. Further, the read pixel signal is already subjected to the 2×2 binning processing. Therefore, the number of pixels to be later processed in each of the A/D conversion, the averaging processing, and the digital binning processing can be reduced to a ¼ level, compared to the above-described 1×1 case. The processing speed becomes higher and a high frame rate can be realized.

In general, in the analog signal based pixel addition processing, for example, if anyone of 2×2 pixels is defective or when the pixel addition circuit 120 is malfunctioned, the pixels subjected to the addition processing are regarded as defective pixels. However, according to the present exemplary embodiment, the analog signal based pixel addition in the sensor and the digital binning using only the pixel information of normal pixels based on the defective pixel positional information are both performed. Therefore, it is feasible to obtain a pixel addition result that does not include any defective pixel while realizing high-speed reading.

The present exemplary embodiment is not limited to the above-described example. For example, it is useful to change the method or timing for reading defective pixel positional information from a memory and storing the readout information in a buffer.

Figure 10B:
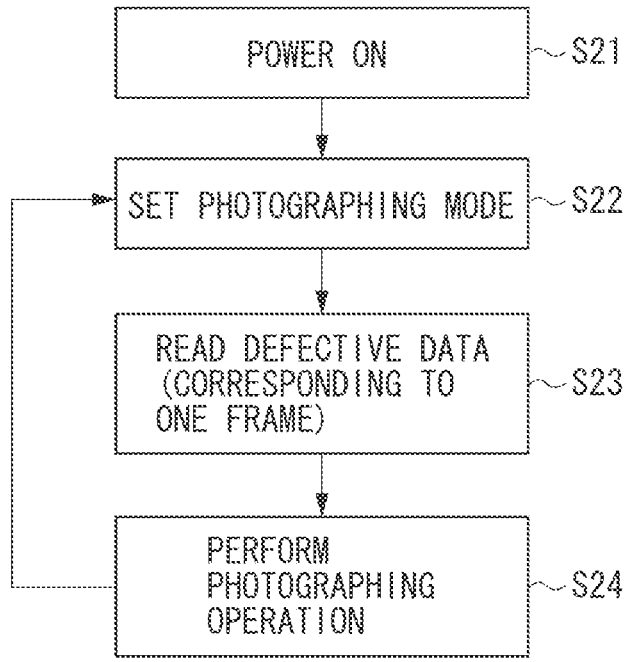

FIG. 10B illustrates another example of a processing flowchart according to the present exemplary embodiment.

According to the example illustrated in FIG. 10B, in step S21, the power source of the imaging apparatus is turned on. Then, in step S22, a photographing mode is set. Subsequently, in step S23, defective pixel positional information of one frame that is preferable for the photographing mode is read out from the memory 124. The read defective pixel positional information is stored in the defective information storage buffer 128 of the photographing control unit 109.

In step S24, a photographing operation including the digital binning processing is performed. In this case, the defective pixel positional information is read out from the defective information storage buffer 128 and the digital binning processing is performed.

When the above-described processing is performed, the photographing control unit 109 accesses the memory 124 provided outside only when the photographing mode is switched and no access to the memory 124 is performed during the digital binning processing. Thus, it is feasible to increase the processing speed of the circuit during the photographing operation.

However, according to the example illustrated in FIG. 10B, it is necessary to prepare the defective information storage buffer 128 that can store defective pixel positional information of at least one frame in the photographing control unit 109. Further, a significant time is required to read the defective pixel positional information when the photographing mode is changed. Therefore, compared to the example illustrated in FIG. 10A, it takes a longer time to change the photographing mode after completing the photographing operation and start a new photographing operation.

Figure 10C:
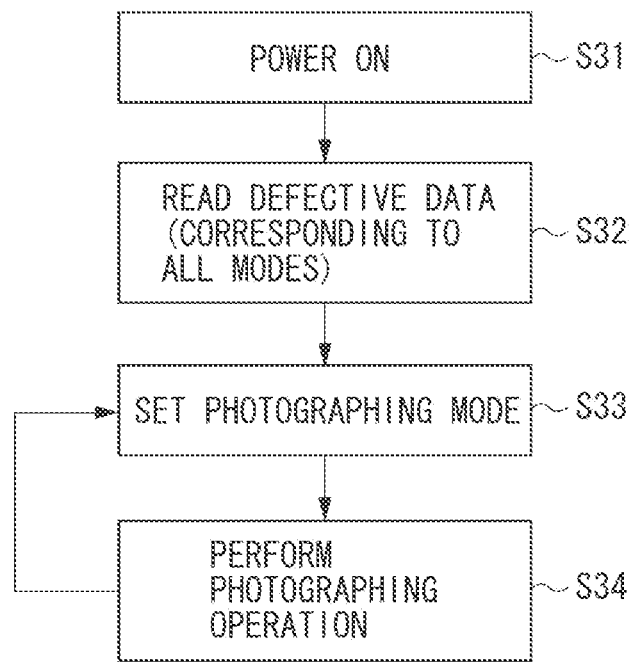

FIG. 10C illustrates another example of the processing flowchart according to the present exemplary embodiment.

According to the example illustrated in FIG. 10C, in step S31, the power source of the imaging apparatus is turned on. Then, in step S32, defective pixel positional information corresponding to all photographing modes is read out from the memory 124. The read defective pixel positional information is stored in the defective information storage buffer 128 of the photographing control unit 109.

In step S33, a photographing mode is set. Then, in step S34, a photographing operation including the digital binning processing is performed. In this case, the defective pixel positional information is read out from the defective information storage buffer 128 and the digital binning processing is performed.

According to the above-described processing, no access to the memory 124 is performed during the digital binning processing. Therefore, it is feasible to increase the processing speed of the circuit during the photographing operation. Further, no memory access is required when the photographing mode is changed. Therefore, the time required to change the photographing mode after completing the photographing operation and to start a new photographing operation can be reduced. However, the circuit scale becomes larger because it is necessary to prepare the defective information storage buffer 128 that can store the defective information corresponding to all photographing modes in the photographing control unit 109.

Further, the present invention can be realized by the following processing. More specifically, the processing includes providing a software program that can realize the functions of the above-described exemplary embodiment to a system or an apparatus via a network or an appropriate storage medium and causing a computer (or a CPU or a micro-processing unit (MPU)) of the system or the apparatus to read and execute the program.

The above-described exemplary embodiments are mere examples that can realize the present invention. The technical scope of the present invention should not be limited to the above-described embodiments. More specifically, the present invention can be modified in various ways without departing from the technical idea or essential features thereof.

The exemplary embodiment of the present invention has an object to provide an imaging apparatus and an imaging method that can efficiently execute averaging processing and digital binning processing on pixel signals having been non-destructively read out for each pixel. According to the above-described exemplary embodiment, it is feasible to provide an imaging apparatus and an imaging method that can efficiently execute the averaging processing and the digital binning processing on the pixel signals having been read plural times for each pixel, with a smaller circuit scale, without increasing the reading time or the processing time.

Aspects of the present invention can also be realized by a computer of a system or apparatus (or devices such as a CPU or MPU) that reads out and executes a program recorded on a memory device (computer-readable medium) to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable medium). In such a case, the system or apparatus, and the recording medium where the program is stored, are included as being within the scope of the present invention.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2012-020030 filed Feb. 1, 2012, which is hereby incorporated by reference herein in its entirety.

What is claimed is:

1. An imaging apparatus, comprising:
a sensor including a plurality of pixels arranged in a two-dimensional pattern, wherein each of the plurality of pixels includes a photoelectric conversion element, and a sample-hold circuit configured to sample and hold a signal based on an electric charge of the photoelectric conversion element;
a control unit configured to sample and hold the signal for a plurality of sample-hold circuits of the plurality of pixels, to perform a plurality of non-destructive reading operations for the signal having been sampled and held by the sample-hold circuits of one row, and to subsequently perform a plurality of non-destructive reading operations for the signal having been sampled and held by the sample-hold circuit of the next row;
an A/D conversion unit configured to perform analog/digital conversion processing on signals read by the plurality of non-destructive reading operations from a sample-hold circuit of the plurality of sample-hold circuits;

an averaging processing unit configured to perform averaging processing on the signals having been analog/digital converted by the A/D conversion unit; and a digital binning unit configured to perform binning processing using a signal having been averaging processed by the averaging processing unit.

2. The imaging apparatus according to claim 1, further comprising:

a storage unit configured to temporarily store defective pixel positional information, wherein the digital binning unit is configured to perform the binning processing based on the defective pixel positional information stored in the storage unit, using signals that do not include any defective pixel signals indicated by the defective pixel positional information.

3. The imaging apparatus according to claim 2, wherein the defective pixel positional information to be stored in the storage unit is stored in an external memory.

4. The imaging apparatus according to claim 3, wherein the defective pixel positional information stored in the storage unit is changeable according to a setting state of the imaging apparatus.

5. The imaging apparatus according to claim 3, wherein a plurality of pieces of the defective pixel positional information that corresponds to respective photographing modes of the imaging apparatus is stored in the external memory.

6. The imaging apparatus according to claim 3, wherein the defective pixel positional information is read out from the external memory each time the digital binning unit performs the binning processing.

7. The imaging apparatus according to claim 3, wherein the defective pixel positional information is read out from the external memory when a photographing mode of the imaging apparatus is set.

8. The imaging apparatus according to claim 3, wherein a plurality of pieces of the defective pixel positional information is read out from the external memory when a power source of the imaging apparatus is turned on.

9. The imaging apparatus according to claim 1, wherein the averaging processing unit and the digital binning unit are provided on a same semiconductor apparatus.

10. The imaging apparatus according to claim 9, further comprising:

a plurality of semiconductor apparatuses on which the averaging processing unit and the digital binning unit are provided, wherein the plurality of semiconductor apparatuses is respectively allocated to mutually different partial regions of an imaging region in which the plurality of pixels is provided.

11. The imaging apparatus according to claim 1, wherein the averaging processing unit includes a buffer that has a capacitance capable of storing input signals of one row.

12. The imaging apparatus according to claim 1, wherein the sensor is constituted by a plurality of semiconductor substrates each including a plurality of pixels, wherein each of the plurality of pixels comprises an amplifier that outputs a signal based on an electric charge of the photoelectric conversion element, and wherein the sample-hold circuit samples and holds the signal outputted from the amplifier.

13. The imaging apparatus according to claim 1, wherein the sensor includes a pixel addition circuit configured to add analog signals from a plurality of pixels as a signal of one pixel, wherein the A/D conversion unit is configured to perform the analog/digital conversion processing on the signals obtained by the pixel addition circuit.

14. The imaging apparatus according to claim 1, wherein the sensor includes:

a pixel addition circuit configured to add analog signals from a plurality of pixels as a signal of one pixel; and an amplification unit configured to amplify the signal having been processed by the analog binning unit, wherein the A/D conversion unit is configured to perform the analog/digital conversion processing on the signal amplified by the amplification unit.

15. The imaging apparatus according to claim 1, further comprising:

a storage unit configured to temporarily store defective pixel positional information, wherein the digital binning unit is configured to perform binning processing based on the defective pixel positional information stored in the storage unit, using signals that do not include any defective pixel signals indicated by the defective pixel positional information, of signals having been subjected to the averaging processing performed by the averaging processing unit, wherein the sensor is constituted by a plurality of semiconductor substrates each including a plurality of pixels, and wherein a plurality of pieces of the defective pixel positional information that corresponds to respective photographing modes of the imaging apparatus is stored in an external memory.

16. The imaging apparatus according to claim 1, further comprising:

a storage unit configured to temporarily store defective pixel positional information, wherein the digital binning unit is configured to perform binning processing based on the defective pixel positional information stored in the storage unit, using signals that do not include any defective pixel signals indicated by the defective pixel positional information, of signals having been subjected to the averaging processing performed by the averaging processing unit, wherein a plurality of pieces of the defective pixel positional information that corresponds to respective photographing modes of the imaging apparatus is stored in an external memory, and wherein the defective pixel positional information that corresponds to a photographing mode setting in the imaging apparatus is read out from the external memory to the storage unit.

17. An imaging method for an imaging apparatus that includes a sensor including a plurality of pixels arranged in a two-dimensional pattern, wherein each of the plurality of pixels includes a photoelectric conversion element, and a sample-hold circuit configured to sample and hold a signal based on an electric charge of the photoelectric conversion element, and a control unit configured to sample and hold the signal for a plurality of sample-hold circuits of the plurality of pixels, to perform a plurality of non-destructive reading operations for the signal having been sampled and held by the sample-hold circuits of one row, and to subsequently perform a plurality of non-destructive reading operations for the signal having been sampled and held by the sample-hold circuit of the next row, the method comprising:

performing analog/digital conversion processing on signals read by the plurality of non-destructive operations from a sample-hold circuit of the plurality of sample-hold circuits;

performing averaging processing on the analog/digital converted signal; and performing digital binning processing using the averaging processed signal.

18. An imaging apparatus comprising:
a sensor including a plurality of pixels arranged in a two-dimensional pattern, wherein each of the plurality of pixels includes a photoelectric conversion element, an amplifier that outputs a signal based on an electric charge of the photoelectric conversion element, and a sample-hold circuit that samples and holds the signal output from the amplifier;
a control unit configured to perform batch sampling and holding the signal for a plurality of sample-hold circuits of the plurality of pixels, to perform a plurality of non-destructive reading operations for the signal having been sampled and held by the sample-hold circuits of one row, and to subsequently perform a plurality of non-destructive reading operations for the signal having been sampled and held by the sample-hold circuit of the next row;
an averaging processing unit configured to perform averaging processing on the signals read by the plurality of non-destructive reading operations from a sample-hold circuit of the plurality of sample-hold circuits; and
a binning unit configured to perform binning processing using a signal having been averaging processed by the averaging processing unit.

19. The imaging apparatus according to claim 18, further comprising:
an A/D conversion unit configured to perform analog/digital conversion processing on signals read by the plurality of non-destructive reading operations,
wherein the averaging processing unit is configured to perform the averaging processing on the signals having been analog/digital converted by the A/D conversion unit, for each pixel, and
wherein the binning unit is configured to perform the binning processing using a signal having been averaging processed by the averaging processing unit.

20. An imaging apparatus comprising:
a sensor including a plurality of pixels arranged in a two-dimensional pattern, wherein each of the plurality of pixels includes a photoelectric conversion element, and a sample-hold circuit that samples and holds a signal based on an electric charge of the photoelectric coversion element;
a control unit configured to perform batch sampling and holding the signal for a plurality of sample-hold circuits of the plurality of pixels, to perform a plurality of non-destructive reading operations for the signal having been sampled and held by the sample-hold circuits of one row, and to subsequently perform a plurality of non-destructive reading operations for the signal having been sampled and held by the sample-hold circuit of the next row;
an averaging processing unit configured to perform averaging processing on the signals read by the plurality of non-destructive reading operations from a sample-hold circuit of the plurality of sample-hold circuits; and
a binning unit configured to perform binning processing using a signal having been averaging processed by the averaging processing unit.

21. The imaging apparatus according to claim 20,
wherein each of the plurality of pixels further comprises an amplifier that outputs a signal based on an electric charge of the photoelectric conversion element, and
wherein the sample-hold circuit samples and holds the signal outputted from the amplifier.

22. The imaging apparatus according to claim 20, further comprising:
an A/D conversion unit configured to perform analog/digital conversion processing on signals read by the plurality of non-destructive reading operations,
wherein the averaging processing unit is configured to perform the averaging processing on the signals having been analog/digital converted by the A/D conversion unit, for each pixel, and
wherein the binning unit is configured to perform the binning processing using a signal having been averaging processed by the averaging processing unit.

* * * * *